United States Patent
Kang et al.

(10) Patent No.: US 10,789,335 B2
(45) Date of Patent: Sep. 29, 2020

(54) REMOTE DIAGNOSIS MANAGEMENT SYSTEM AND METHOD FOR OPERATING THE SAME

(71) Applicant: DARTPOINT TECH. CO., LTD., Taipei (TW)

(72) Inventors: Chi-Lin Kang, New Taipei (TW); Ai-Chieh Lu, New Taipei (TW); Chao-Yuan Huang, Taipei (TW)

(73) Assignee: DARTPOINT TECH. CO., LTD., Taipei (TW)

( * ) Notice: Subject to any disclaimer, the term of this patent is extended or adjusted under 35 U.S.C. 154(b) by 931 days.

(21) Appl. No.: 15/361,018

(22) Filed: Nov. 24, 2016

(65) Prior Publication Data

US 2017/0161463 A1  Jun. 8, 2017

Related U.S. Application Data

(60) Provisional application No. 62/264,345, filed on Dec. 8, 2015.

(30) Foreign Application Priority Data

Oct. 5, 2016  (TW) .............................. 105132242 A (51) Int. Cl.
*A61H 33/00* (2006.01)
*G06F 19/00* (2018.01)
(Continued)

(52) U.S. Cl.
CPC ......... *G06F 19/3481* (2013.01); *A61H 33/00* (2013.01); *G16H 40/63* (2018.01); *G16H 50/20* (2018.01); *A61H 2033/0079* (2013.01)

(58) Field of Classification Search
CPC ............ A61H 2033/0079; A61H 33/00; A61H 33/005
See application file for complete search history.

(56) References Cited

U.S. PATENT DOCUMENTS 5,117,233 A * 5/1992 Hamos .................. A61H 33/60
                                                                    340/12.22
8,280,535 B2   10/2012 Hsieh
(Continued)

FOREIGN PATENT DOCUMENTS

CN  101753364 A   6/2010
CN  101821720 A   9/2010
(Continued)

*Primary Examiner* — LaToya M Louis
(74) *Attorney, Agent, or Firm* — Mark M. Friedman (57) ABSTRACT

A remote diagnosis management system is utilized for a plurality of massage bath devices and includes at least one processor executing steps of: receiving a remote trigger event of each of the massage bath devices, wherein the remote trigger event is generated by a control unit of each of the massage bath devices or by at least one of a maintenance-worker and a user of each of the massage bath devices; analyzing the remote trigger event to generate an analyzed result; remotely operating at least one state of each of the massage bath devices according to the analyzed result; requesting authorization from the user of each of the massage bath devices before the step of remotely operating the at least one state of each of the massage bath devices; and scheduling at least one remote diagnosis of the massage bath devices.

15 Claims, 9 Drawing Sheets

(51) Int. Cl.
*G16H 40/63* (2018.01)
*G16H 50/20* (2018.01)

(56) References Cited

U.S. PATENT DOCUMENTS

| | | |
|---|---|---|
| 10,224,623 B1 * | 3/2019 | Spears .................. H05B 45/00 |
| 2009/0132066 A1 | 5/2009 | Hollaway |
| 2010/0093401 A1 | 4/2010 | Moran et al. |
| 2012/0304374 A1 * | 12/2012 | Amendt ............... A61N 5/0625 |
| | | 4/524 |
| 2015/0238384 A1 * | 8/2015 | Macey ................ H04L 12/2825 |
| | | 700/282 |
| 2015/0322652 A1 | 11/2015 | Mazz et al. |
| 2015/0335523 A1 | 11/2015 | Kang et al. |
| 2015/0335524 A1 | 11/2015 | Kang et al. |
| 2016/0175189 A1 * | 6/2016 | Fils ........................ G06F 3/165 |
| | | 700/94 |

FOREIGN PATENT DOCUMENTS

| | | |
|---|---|---|
| CN | 102829552 A | 12/2012 |
| CN | 203705971 U | 7/2014 |
| CN | 205812088 U | 12/2016 |
| EP | 2202594 A2 | 6/2010 |
| KR | 200442284 Y | 10/2008 |
| TW | 498357 | 4/2015 |
| TW | 201545060 | 12/2015 |

\* cited by examiner

REMOTE DIAGNOSIS MANAGEMENT SYSTEM AND METHOD FOR OPERATING THE SAME

CROSS REFERENCE TO RELATED APPLICATION

This patent application claims priority of U.S. Provisional Application Ser. No. 62/264,345, entitled "Several Controlling Systems for bathing system and methods related to the controlling Systems", which is filed on Dec. 8, 2015, incorporated herein by reference.

BACKGROUND OF THE INVENTION

Field of Invention

The present invention relates to a massage bathe equipment field, and more particularly to a remote diagnosis management system and a method for operating the same.

Description of Prior Art

Currently, when a bath system is abnormal, a maintenance provider only can diagnose the bath system remotely. The maintenance provider cannot remotely control, manage, or maintain a massage bath equipment of the bath system according to a diagnosis result. That is, services that the maintenance provider can provide for the massage bath equipment are fewer.

Consequently, there is a need to provide a remote diagnosis management system to solve the above-mentioned problem in the prior art.

SUMMARY OF THE INVENTION

The present invention provides a remote diagnosis management system and a method for operating the same which can provide more services for massage bath equipment.

A remote diagnosis management system of the present invention is utilized for at least one massage bath equipment. The remote diagnosis management system includes a communication module configured to receive a remote trigger event of the at least one massage bath equipment; an analyzing module configured to analyze the remote trigger event to generate an analyzed result; and a processing module configured to remotely operate at least one state of the at least one massage bath equipment according to the analyzed result.

A remote diagnosis management system of the present invention is utilized for at least one massage bath equipment. The remote diagnosis management system includes a communication module configured to receive a remote trigger event of the at least one massage bath equipment; an analyzing module configured to analyze the remote trigger event to generate an analyzed result; a processing module configured to control, according to the analyzed result, a control terminal to remotely operate at least one state of the at least one massage bath equipment; and a display module configured to display, in real time, the at least one state of the at least one massage bath equipment and/or an operable interface.

A method for operating a remote diagnosis management system of the present invention is utilized for at least one massage bath equipment. The method for operating the remote diagnosis management system includes receiving a remote trigger event of the at least one massage bath equipment; analyzing the remote trigger event to generate an analyzed result; and operating at least one state of the at least one massage bath equipment remotely according to the analyzed result.

A method for operating a remote diagnosis management system of the present invention is utilized for at least one massage bath equipment. The method for operating the remote diagnosis management system includes receiving a remote trigger event of the at least one massage bath equipment; analyzing the remote trigger event to generate an analyzed result; controlling, according to the analyzed result, a control terminal to operate at least one state of the at least one massage bath equipment remotely; and displaying, in real time, the at least one state of the at least one massage bath equipment and/or an operable interface on a remote diagnosis terminal.

The remote diagnosis management system and the method for operating the same of the present invention can provide more services for the at least one massage bath equipment according to the analyzed result of the remote trigger event.

DETAILED DESCRIPTION OF THE PREFERRED EMBODIMENTS

Figure 1:
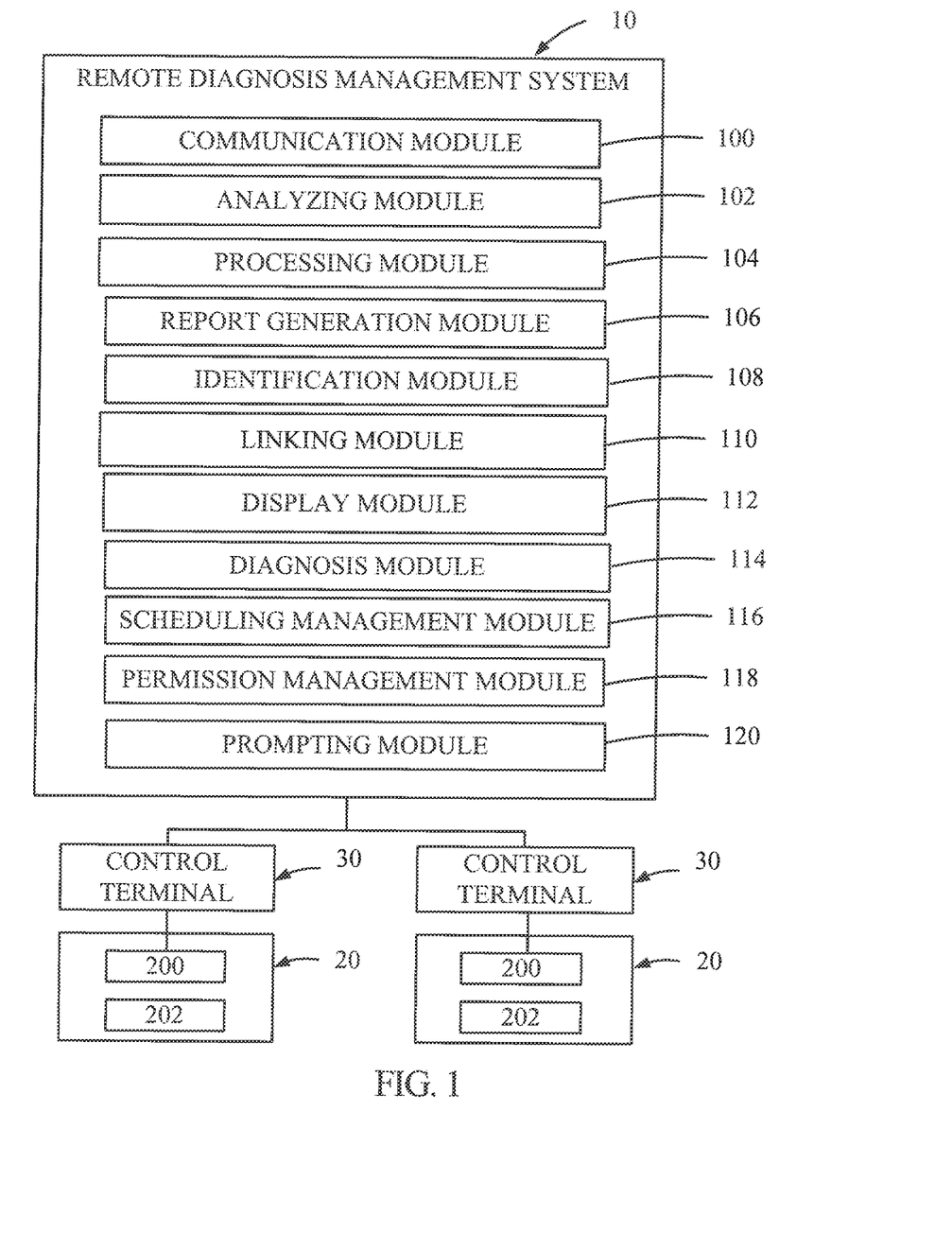
FIG. 1 is a block diagram of a remote diagnosis management system in accordance with an embodiment of the present invention.

Please refer to FIG. 1. FIG. 1 is a block diagram of a remote diagnosis management system 10 in accordance with an embodiment of the present invention.

The remote diagnosis management system 10 is utilized for at least one massage bath equipment 20 and can remotely manage the at least one massage bath equipment 20 and provide at least one service for the at least one massage bath equipment 20. The remote diagnosis management system 10 at least includes a communication module 100, an analyzing module 102, and a processing module 104.

The communication module 100 is configured to receive a remote trigger event of the at least one massage bath equipment 20. The remote trigger event may be generated by a user of the at least one massage bath equipment 20, a maintenance worker of the at least one massage bath equipment 20, or a control unit 200 of the at least one massage bath equipment 20.

The analyzing module 102 is configured to analyze the remote trigger event to generate an analyzed result.

The processing module 104 is configured to remotely operate at least one state of the at least one massage bath equipment 20 according to the analyzed result.

The remote diagnosis management system 10 further includes a report generation module 106. The report generation module 106 is configured to generate a report of the at least one state of the at least one massage bath equipment 20 and/or a maintenance record of the at least one massage bath equipment 20.

The remote diagnosis management system 10 further includes an identification module 108. The identification module 108 is configured to request authorization from the user of the at least one massage bath equipment 20, before the processing module 104 remotely operates the at least one state of the at least one massage bath equipment 20, and/or is configured to identify whether authentication of the at least one massage bath equipment 20 is valid when the at least one massage bath equipment 20 is linked to the remote diagnosis management system 10.

The remote diagnosis management system 10 further includes a linking module 110. The linking module 110 is configured to set up a link between the at least one massage bath equipment 20 and the remote diagnosis management system 10 and/or a link between a user application (APP) and the remote diagnosis management system 10.

The remote diagnosis management system 10 further includes a display module 112. The display module 112 is configured to display, in real time, the at least one state of the at least one massage bath equipment 20 and/or an operable interface. The at least one state may be a state (e.g., a temperature) which is displayed on a display panel 202 of the at least one massage bath equipment 20, or may be a state which is not displayed on the display panel 202. The maintenance worker of the at least one massage bath equipment 20 can control the at least one massage bath equipment 20 via the operable interface.

The remote diagnosis management system 10 further includes a diagnosis module 114. The diagnosis module 114 is configured to diagnose the at least one state of the at least one massage bath equipment 20 remotely.

The remote diagnosis management system further includes a scheduling management module 116. The scheduling management module 116 is configured to schedule at least one remote diagnosis of the at least one massage bath equipment 20.

The remote diagnosis management system 10 further includes a permission management module 118. The permission management module 118 is configured to manage a scope which the remote diagnosis management system 10 is permitted to manage.

The remote diagnosis management system 10 further includes a prompting module 120, The prompting module 120 is configured to remotely provide information related to the remote trigger event and configured to remotely display the information related to the remote trigger event.

Figure 4:
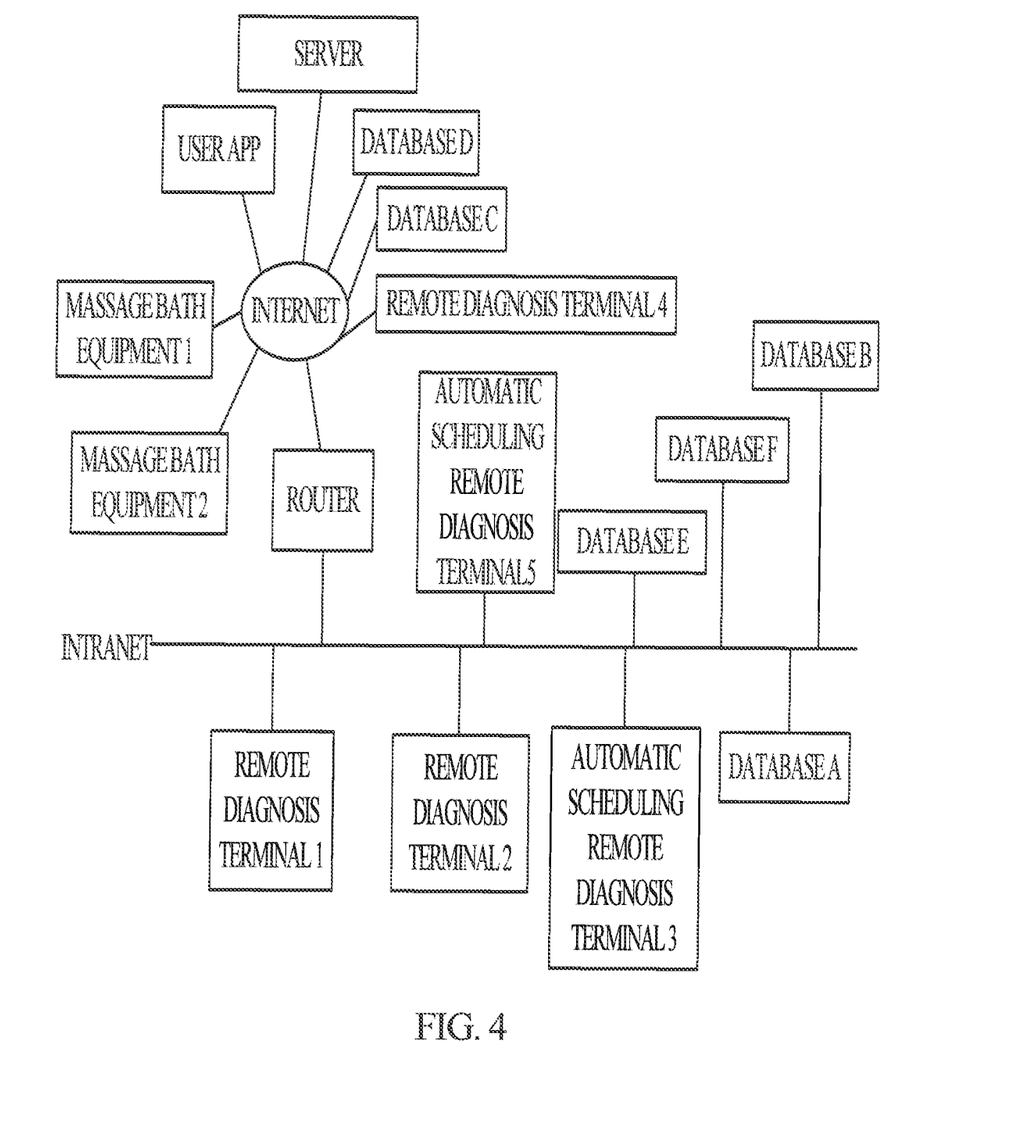
FIG. 4 is an architecture diagram of relations among massage bath equipment, remote diagnosis terminals, and databases in accordance with an embodiment of the present invention.

In another embodiment, the processing module 104 is configured to control a control terminal 30 to remotely operate the at least one state of the at least one massage bath equipment 20 according to the analyzed result. The display module 112 is configured to control a remote diagnosis terminal (as shown in FIG. 2 and FIG. 4) to display, in real time, the at least one state of the at least one massage equipment 20 and/or the operable interface.

Figure 2:
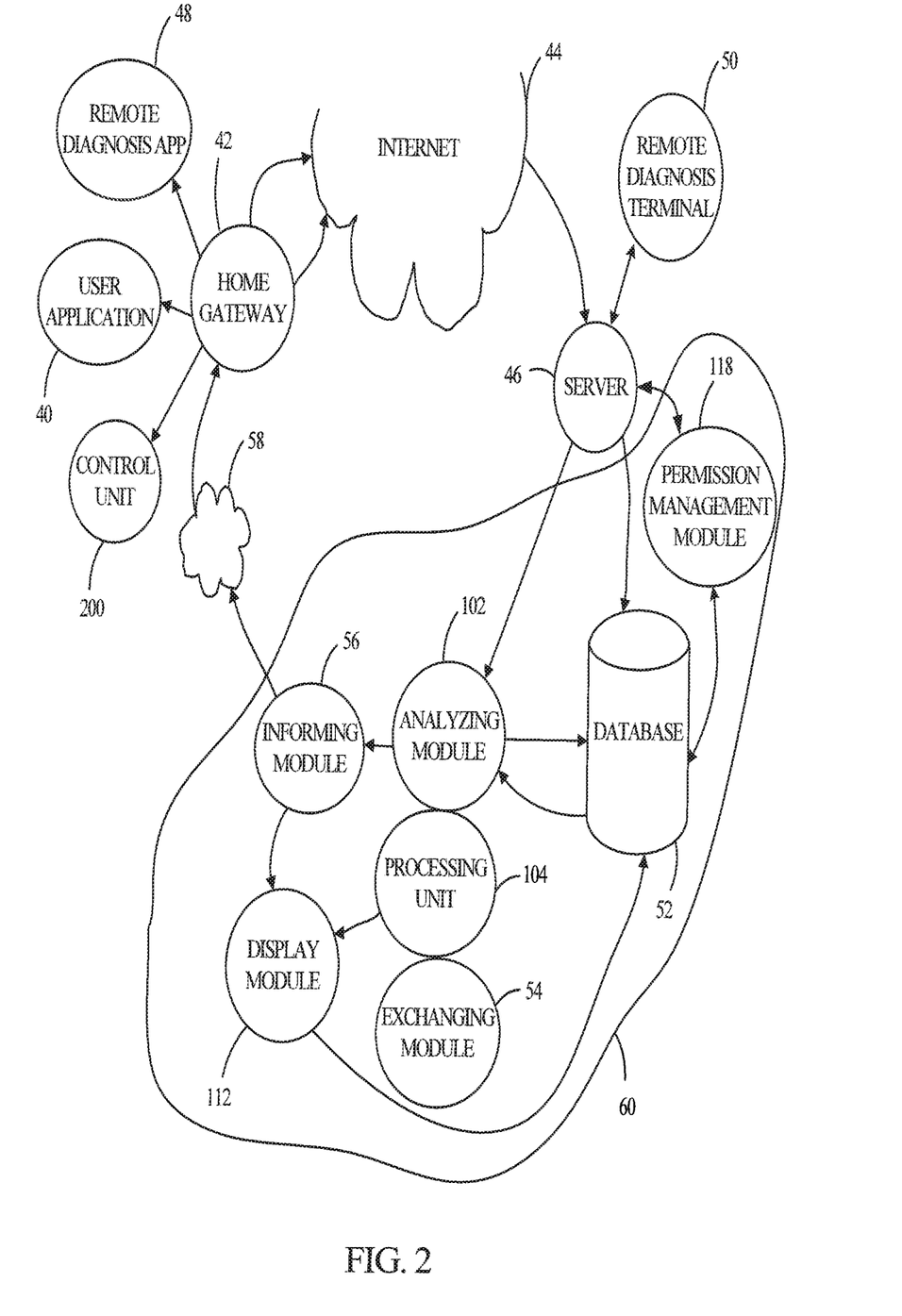
FIG. 2 is a relation diagram of the remote diagnosis management system in accordance with an embodiment of the present invention.

Please refer to FIG. 1 and FIG. 2. FIG. 2 is a relation diagram of the remote diagnosis management system 10 in accordance with an embodiment of the present invention.

The remote trigger event may be generated by the user of the at least one massage bath equipment 20 via a user application 40. The user application 40 may be installed in a mobile device. For example, the user transmits a desired service request to a server (a maintenance provider of the at least one massage bath equipment 20) 46 via a home gateway 42 and internet 44.

Alternatively, the remote trigger event may be generated by the maintenance worker of the at least one massage bath equipment 20 via a remote diagnosis application 48. The remote diagnosis application 48 may be installed in one of a notebook, a tablet, a mobile phone, a desktop computer, a server, and an electronic device including a microprocessor. For example, the maintenance worker transmits a desired service request for maintaining the at least one massage bath equipment 20 to the server 46 via the home gateway 42 and the internet 44.

Alternatively, the remote trigger event may be generated by the control unit 200 of the at least one massage bath equipment 20. For example, the control unit 200 transmits the at least one state of the at least one massage bath equipment 20 to the server 46 via the home gateway 42 and the internet 44.

After the server 46 receives the remote trigger event, the remote diagnosis terminal 50 communicates with the permission management module 118 via the server 46. The permission management module 118 determines whether the remote trigger event is in the scope which the remote diagnosis management system 10 is permitted to manage and/or determines whether the at least one massage bath equipment 20 is a target which is maintained by the remote diagnosis management system 10. Furthermore, after receiving the remote trigger event, the server 46 stores at least one record related to the remote trigger event into a database 52.

When the permission management module 118 determines that the remote trigger event is in the scope which the remote diagnosis management system 10 is permitted to manage and/or determines that the at least one massage bath equipment 20 is the target which is maintained by the remote diagnosis management system 10, the server 46 transmits the remote trigger event to the analyzing module 102. After analyzing the remote trigger event, the analyzing module 102 transmits the analyzed result to an informing module 56 and the processing module 104. The informing module 56 transmits the analyzed result to the user application 40 via the internet 58, the remote diagnosis application 48, or the control unit 200. The processing module 104 may transmit the analyzed result to the display module 112 for display.

In another embodiment, a remote diagnosis terminal 60 includes the permission management module 118. As a result, the remote diagnosis terminal 60 may determine, by itself, whether the remote trigger event is in the scope which the remote diagnosis management system 10 is permitted to manage and/or determine whether the at least one massage bath equipment 20 is the target which is maintained by the remote diagnosis management system 10.

In summary, a difference between the remote diagnosis terminal 50 and the remote diagnosis terminal 60 is that the remote diagnosis terminal 60 includes the permission management module 118. That is, the remote diagnosis terminal 50 has to communicate with the permission management module 118 via the server 46 to determine whether the remote trigger event is in the scope which the remote diagnosis management system 10 is permitted to manage and/or to determine whether the at least one massage bath equipment 20 is the target which is maintained by the remote diagnosis management system 10. The remote diagnosis terminal 60 can determine, by itself, whether the remote trigger event is in the scope which the remote diagnosis management system 10 is permitted to manage and/or determine whether the at least one massage bath equipment 20 is the target which is maintained by the remote diagnosis management system 10. The remote diagnosis terminal 50 and the remote diagnosis terminal 60 may share respective data via respective exchanging modules 54.

Furthermore, it is noted that the control terminal 30 in FIG. 1 may be disposed in the remote diagnosis terminals 50 and 60 in FIG. 2. In another embodiment, the control terminal 30 in FIG. 1 may be a remote controller of the at least one massage bath equipment 20 or disposed in the at least one massage bath equipment 20.

Figure 3:
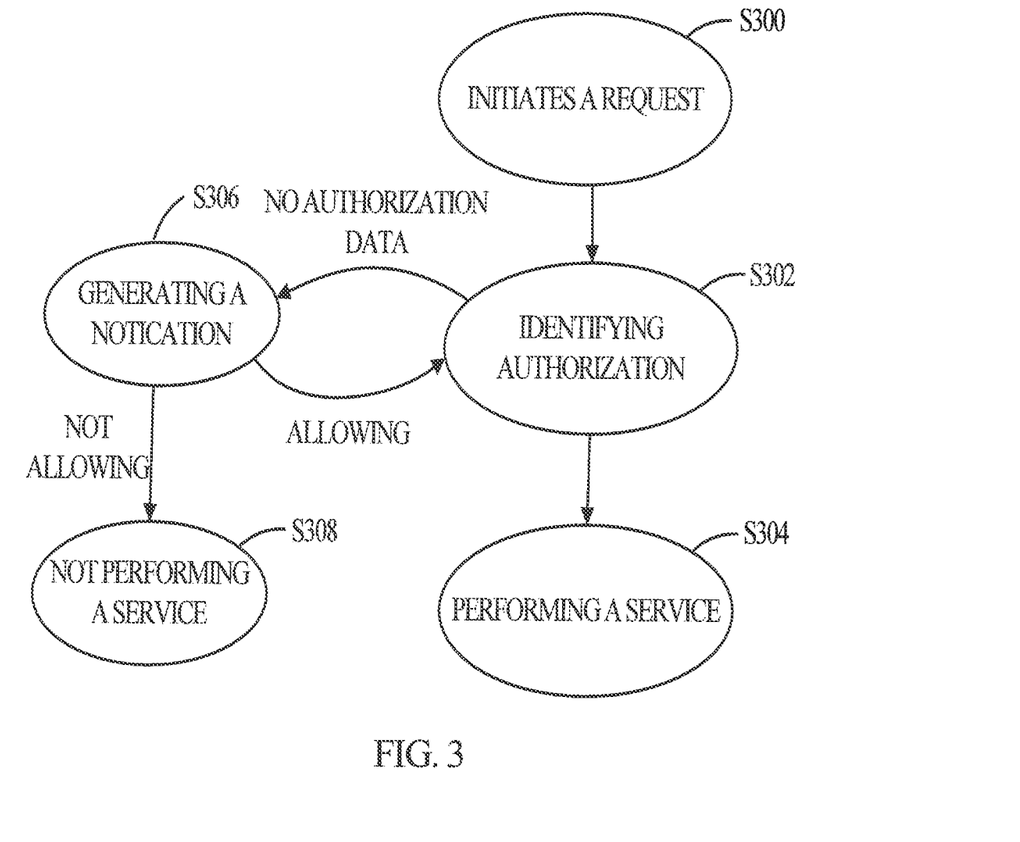
FIG. 3 is a flowchart of acquiring authorization from a user when the remote diagnosis management system provides at least one service for the user.

Please refer to FIG. 1 to FIG. 3. FIG. 3 is a flowchart of acquiring authorization from the user when the remote diagnosis management system 10 provides at least one service (e.g., a routine remote diagnosis) for the user.

In step S300, the remote diagnosis management system 10 initiates a request for providing at least one service.

In step S302, the remote diagnosis management system 10 determines whether the authorization from user has existed. If the authorization from the user has existed, step S304 is performed. If no, step S306 is performed.

In step S304, the remote diagnosis management system 10 performs the at least one service, for example, performs a remote diagnosis.

In step S306, the remote diagnosis management system 10 identifies whether the authorization from the user is acquired via the user applications 40. If the authorization from the user is acquired, step S302 is performed. If no, step S308 is performed.

In step S308, the at least one service is not performed.

Please refer to FIG. 1 to FIG. 4. FIG. 4 is an architecture diagram of relations among massage bath equipment, remote diagnosis terminals, and databases in accordance with an embodiment of the present invention.

In FIG. 4, the massage bath equipment and the user application may be linked to the server via the internet. The server may display an image of a web page. According to demand, plural databases can be used to store classified data. The remote diagnosis terminals 1 and 2 (i.e., maintenance workers) can communicate with the massage bath equipment and a user application via an intranet, a router, and the internet. A remote diagnosis terminal 4 can directly communicate with the massage bath equipment and the user application via the internet. Automatic scheduling remote diagnosis terminals 3 and 5 can perform a remote diagnosis to the massage bath equipment automatically via the intranet, the router, and the intranet.

Figure 5:
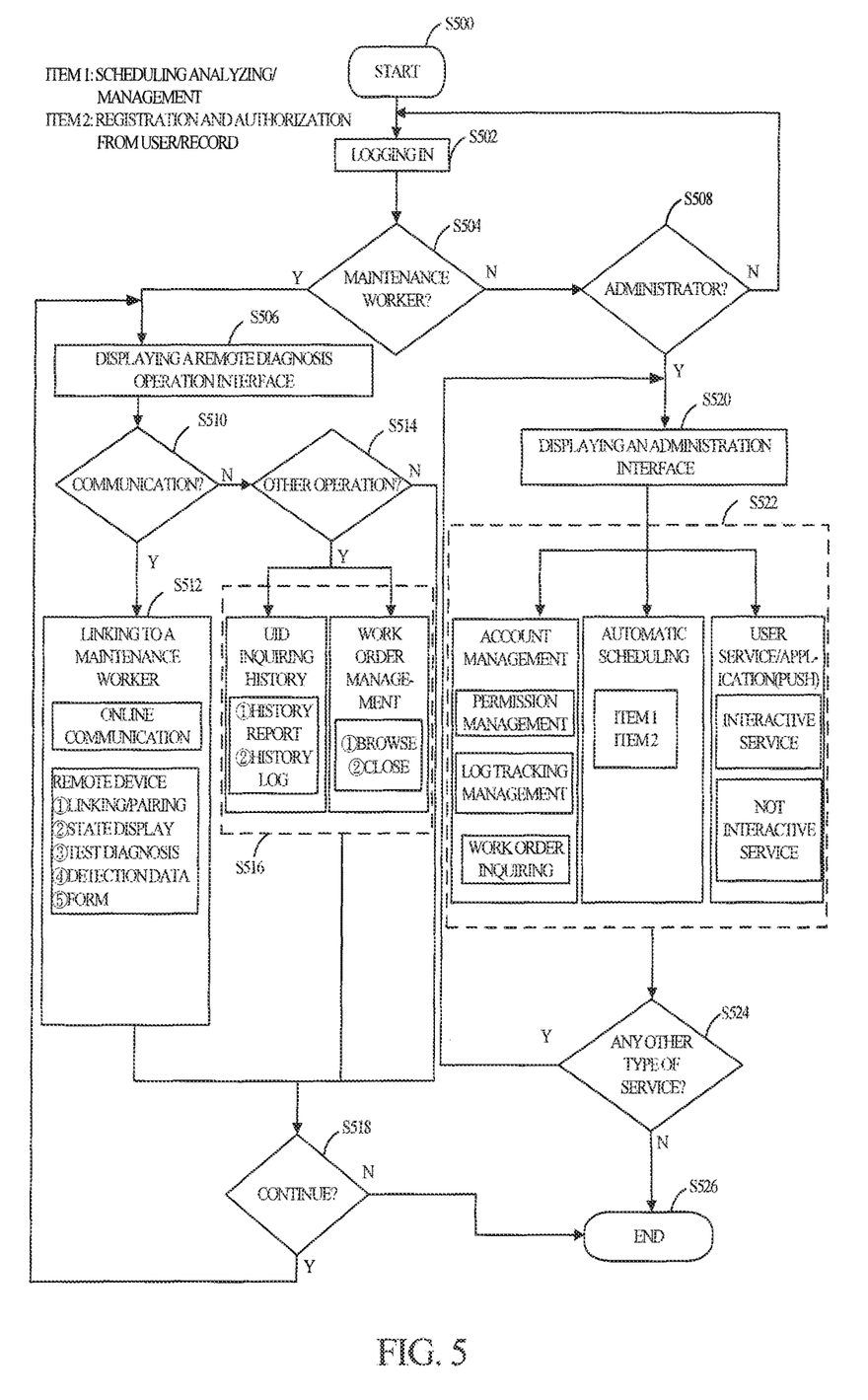
FIG. 5 is a flowchart of logging in the remote diagnosis management system in accordance with an embodiment of the present invention.

Please refer to FIG. 5. FIG. 5 is a flowchart of logging in the remote diagnosis management system in accordance with an embodiment of the present invention.

In step S500, the flowchart starts.

In step S502, an account logs in.

In step S504, it is determined whether the account is a maintenance worker. If yes, step S506 is performed. If no, step S508 is performed.

In step S506, a remote diagnosis operation interface is displayed. Then, step S510 is performed.

In step S508, it is determined whether the account is an administrator. If yes, step S520 is performed. If no, step S502 is performed.

In step S510, it is determined whether to communicate with the at least one massage bath equipment. If yes, step S512 is performed. If no, step S514 is performed.

In step S512, the maintenance worker performs a communication with the at least one massage bath equipment. Then, step S518 is performed. The communication may be but not limited to an online communication with the user, a connection/pairing with the at least one massage bath equipment, a state display, or a test diagnosis, or may be to store detection data or to generate a form.

In step S514, it is determined whether to perform any other operation. If yes, step S516 is performed. If no, step S518 is performed.

In step S516, a diagnosis history or diagnosis management (e.g., work order management) related to the at least one massage bath equipment is inquired. Then, step S518 is performed.

In step S518, it is determined whether the flowchart continues. If yes, returning to step S506. If no, step S526 is performed.

In step S520, an administration interface is displayed. Then, step S522 is performed.

In step S522, account management of maintenance workers, an automatic scheduling, or a user service/an application is performed. Then, step S524 is performed.

In step S524, it is determined whether there is any other type of service. If yes, returning to step S520. If no, step S526 is performed.

Figure 6:
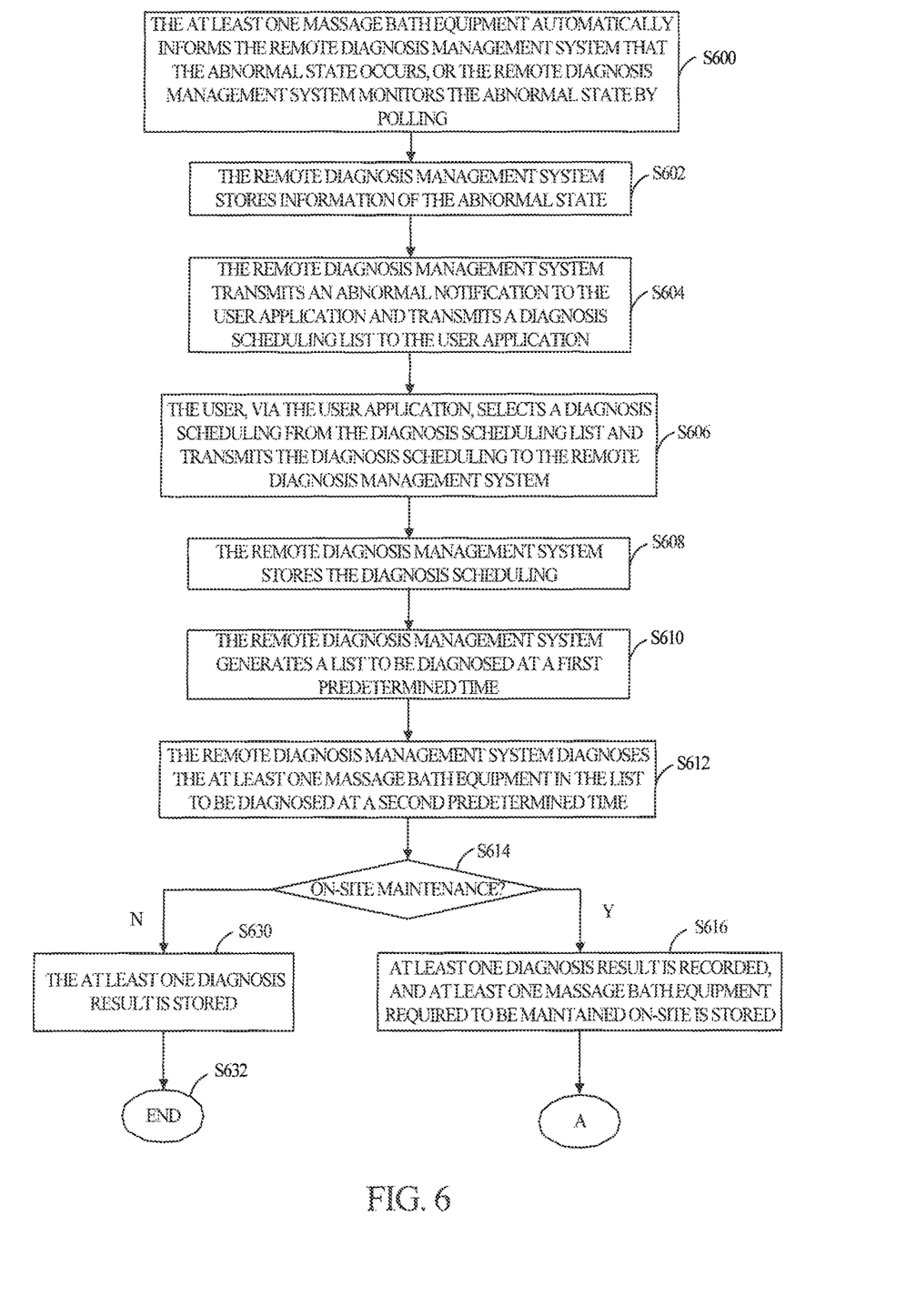
FIGS. 6-7 are a processing flowchart of the remote diagnosis management system in accordance with an embodiment of the present invention when the at least one massage bath equipment has an abnormal state.
Figure 7:
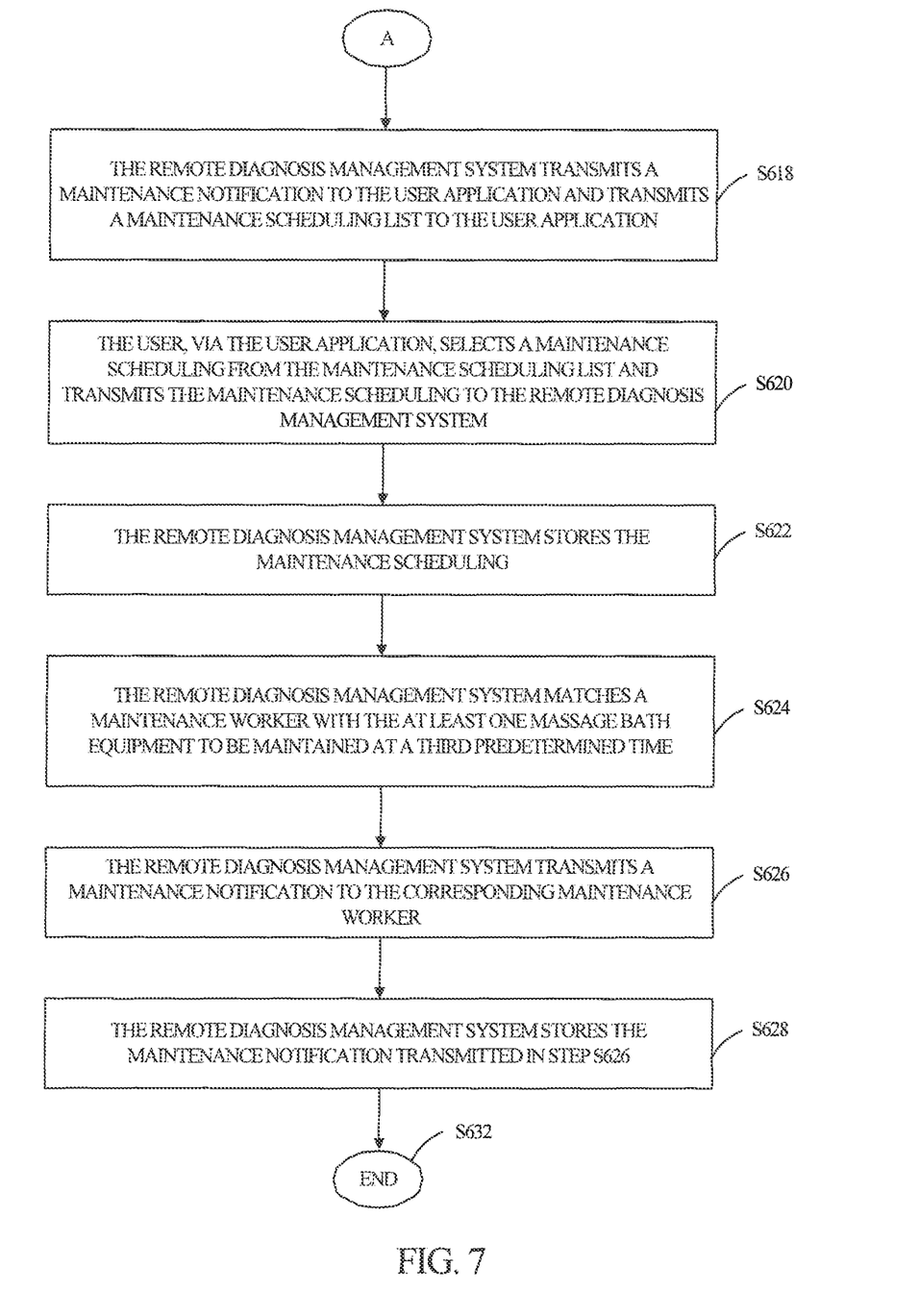

Please refer to FIGS. 1-2 and FIGS. 6-7. FIGS. 6-7 are a processing flowchart of the remote diagnosis management system 10 in accordance with an embodiment of the present invention when the at least one massage bath equipment 20 has an abnormal state. The abnormal state is the above-mentioned remote trigger event.

In step S600, the at least one massage bath equipment automatically informs the remote diagnosis management system 10 that the abnormal state occurs, or the remote diagnosis management system 10 monitors the abnormal state by polling.

In step S602, the remote diagnosis management system 10 stores information of the abnormal state.

In step S604, the remote diagnosis management system 10 transmits an abnormal notification to the user application 40 and transmits a diagnosis scheduling list to the user application 40.

In step S606, the user, via the user application 40, selects a diagnosis scheduling from the diagnosis scheduling list and transmits the diagnosis scheduling to the remote diagnosis management system 10.

In step S608, the remote diagnosis management system 10 stores the diagnosis scheduling.

In step S610, the remote diagnosis management system 10 generates a list to be diagnosed at a first predetermined time (e.g., 10 o'clock every morning).

In step S612, the remote diagnosis management system 10 diagnoses the at least one massage bath equipment 20 in the list to be diagnosed at a second predetermined time (e.g., 3 o'clock every afternoon).

In step S614, it is determined whether onsite maintenance is required. If yes, step S616 is performed. If no, step S630 is performed.

In step S616, at least one diagnosis result is recorded, and at least one massage bath equipment 20 required to be maintained on-site is stored.

In step S618, the remote diagnosis management system 10 transmits a maintenance notification to the user application 40 and transmits a maintenance scheduling list to the user application 40.

In step S620, the user, via the user application 40, selects a maintenance scheduling from the maintenance scheduling list and transmits the maintenance scheduling to the remote diagnosis management system 10.

In step S622, the remote diagnosis management system 10 stores the maintenance scheduling.

In step S624, the remote diagnosis management system 10 matches a maintenance worker with the at least one massage bath equipment 20 to be maintained at a third predetermined time.

In step S626, the remote diagnosis management system 10 transmits a maintenance notification to the corresponding maintenance worker.

In step S628, the remote diagnosis management system 10 stores the maintenance notification transmitted in step S626.

In step S630, the at least one diagnosis result is stored.

In step S632, the flowchart ends.

Figure 8:
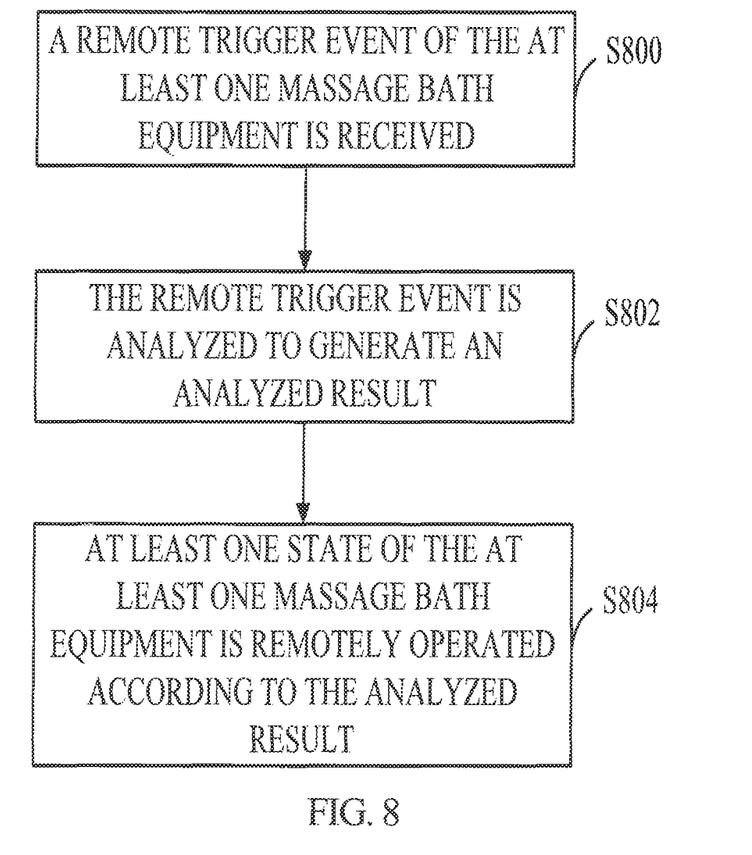
FIG. 8 is a flowchart of a method for operating a remote diagnosis management system in accordance with an embodiment of the present invention.

Please refer to FIG. 8. FIG. 8 is a flowchart of a method for operating a remote diagnosis management system in accordance with an embodiment of the present invention. The method for operating the remote diagnosis management system is utilized for at least one massage bath equipment and includes the following steps.

In step S800, a remote trigger event of the at least one massage bath equipment is received.

In step S802, the remote trigger event is analyzed to generate an analyzed result.

In step S804, at least one state of the at least one massage bath equipment is remotely operated according to the analyzed result.

Figure 9:
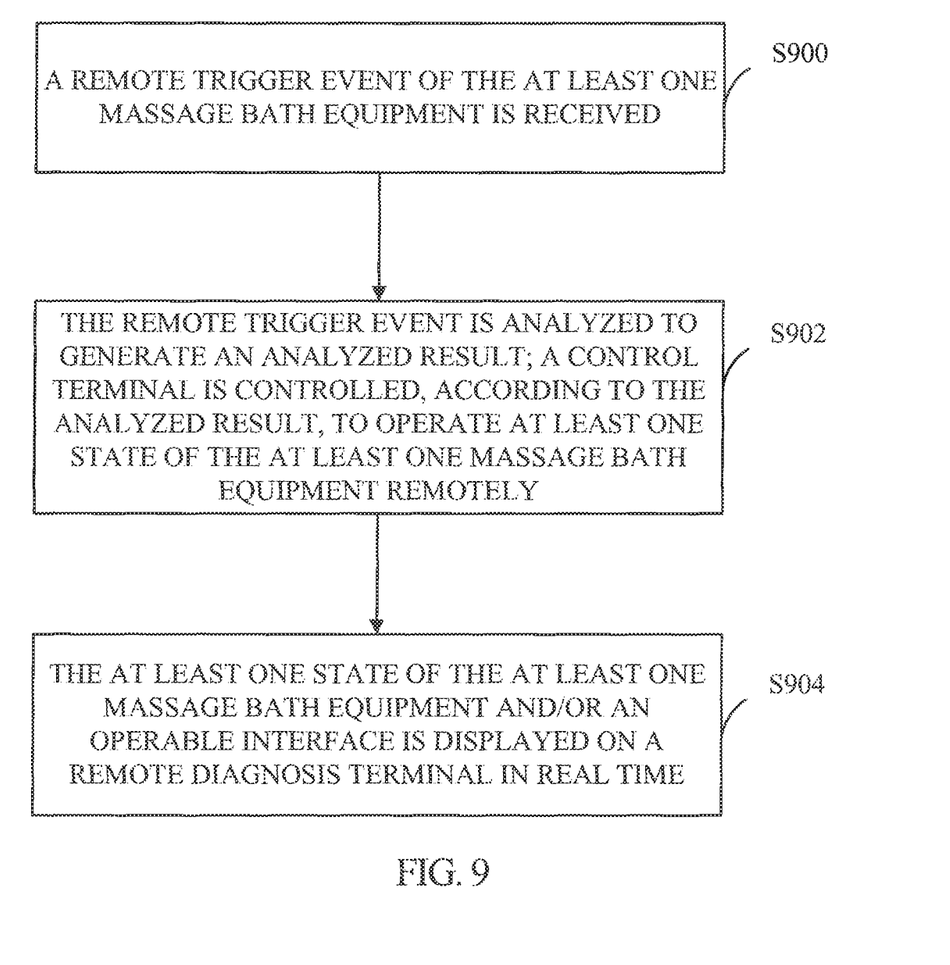
FIG. 9 is a flowchart of a method for operating a remote diagnosis management system in accordance with another embodiment of the present invention.

Please refer to FIG. 9. FIG. 9 is a flowchart of a method for operating a remote diagnosis management system in accordance with another embodiment of the present invention. The method for operating the remote diagnosis management system is utilized for at least one massage bath equipment and includes the following steps.

In step S900, a remote trigger event of the at least one massage bath equipment is received.

In step S902, the remote trigger event is analyzed to generate an analyzed result. A control terminal is controlled, according to the analyzed result, to operate at least one state of the at least one massage bath equipment remotely.

In step S904, the at least one state of the at least one massage bath equipment and/or an operable interface is displayed on a remote diagnosis terminal in real time.

A person skilled in the art can appreciate that all or a part of functions and/or all or a part of steps in the above-mentioned embodiments may be implemented by instructing corresponding hardware with program instructions. Specifically, the remote diagnosis management system of the present invention further includes at least one processor and a memory. The memory is connected to the at least one processor and includes a plurality of program instructions. The at least one processor is configured to execute the program instructions. The program instructions include the above-mentioned modules. The modules are configured to control the at least one processor to perform corresponding functions by executing the program instructions.

As is understood by a person skilled in the art, the foregoing preferred embodiments of the present invention are illustrative rather than limiting of the present invention. It is intended that they cover various modifications and similar arrangements be included within the spirit and scope of the present invention, the scope of which should be accorded the broadest interpretation so as to encompass all such modifications and similar structures.

What is claimed is:

1. A remote diagnosis management system, utilized for a plurality of massage bath devices, the remote diagnosis management system comprising at least one processor executing steps of:
   receiving a remote trigger event of each of the massage bath devices, wherein the remote trigger event is generated by a control unit of each of the massage bath devices or by at least one of a maintenance-worker and a user of each of the massage bath devices;
   analyzing the remote trigger event to generate an analyzed result;
   remotely operating at least one state of each of the massage bath devices according to the analyzed result;
   requesting authorization from the user of each of the massage bath devices before the step of remotely operating the at least one state of each of the massage bath devices; and
   scheduling at least one remote diagnosis of the massage bath devices,
   wherein the at least one processor further executes steps of:
   transmitting a diagnosis scheduling list to a plurality of user applications of the massage bath devices after the step of receiving the remote trigger event of each of the massage bath devices, and then generating a list to be diagnosed according to a plurality of diagnosis schedulings of the massage bath devices that are selected from the diagnosis scheduling list by the users via the user applications, and then diagnosing the massage bath devices that are listed in the list to be diagnosed.

2. The remote diagnosis management system of claim 1, wherein the at least one processor further executes a step of:
   generating a report of the at least one state of each of the massage bath devices and/or a maintenance record of each of the massage bath devices.

3. The remote diagnosis management system of claim 1, wherein the at least one processor further executes a step of:
   identifying whether authentication of each of the massage bath devices is valid when each of the massage bath devices is linked to the remote diagnosis management system.

4. The remote diagnosis management system of claim 1, wherein the at least one processor further executes a step of:
   setting up a link between each of the massage bath devices and the remote diagnosis management system and/or a link between each of the user applications and the remote diagnosis management system.

5. The remote diagnosis management system of claim 1, wherein the at least one processor further executes a step of:
   displaying, in real time, the at least one state of each of the massage bath devices and/or an operable interface.

6. The remote diagnosis management system of claim 1, wherein the at least one processor further executes a step of:
   diagnosing the at least one state of each of the massage bath devices remotely.

7. The remote diagnosis management system of claim 1, wherein the at least one processor further executes a step of:
   determining whether the remote trigger event is in a scope which the remote diagnosis management system is permitted to manage and/or configured to determine whether each of the massage bath devices is a target which is maintained by the remote diagnosis management system.

8. The remote diagnosis management system of claim 1, wherein the at least one processor further executes a step of:
remotely providing information related to the remote trigger event.

9. A remote diagnosis management system, utilized for a plurality of massage bath devices, the remote diagnosis management system comprising at least one processor executing steps of:
receiving a remote trigger event of each of the massage bath devices, wherein the remote trigger event is generated by a control unit of each of the massage bath devices or by at least one of a maintenance-worker and a user of each of the massage bath devices;
analyzing the remote trigger event to generate an analyzed result;
controlling, according to the analyzed result, a control terminal to remotely operate at least one state of each of the massage bath devices;
requesting authorization from the user of each of the massage bath devices before the step of controlling, according to the analyzed result, the control terminal to remotely operate the at least one state of each of the massage bath devices;
displaying, in real time, the at least one state of each of the massage bath devices and/or an operable interface; and
scheduling at least one remote diagnosis of the massage bath devices,
wherein the at least one processor further executes steps of:
transmitting a diagnosis scheduling list to a plurality of user applications of the massage bath devices after the step of receiving the remote trigger event of each of the massage bath devices, and then generating a list to be diagnosed according to a plurality of diagnosis schedulings of the massage bath devices that are selected from the diagnosis scheduling list by the users via the user applications, and then diagnosing the massage bath devices that are listed in the list to be diagnosed.

10. The remote diagnosis management system of claim 9, wherein the at least one processor further executes a step of:
generating a report of the at least one state of each of the massage bath devices and/or a maintenance record of each of the massage bath devices.

11. The remote diagnosis management system of claim 9, wherein the at least one processor further executes a step of:
identifying whether authentication of each of the massage bath devices is valid when each of the massage bath devices is linked to the remote diagnosis management system.

12. The remote diagnosis management system of claim 9, wherein the at least one processor further executes a step of:
setting up a link between each of the massage bath devices and the remote diagnosis management system and/or a link between each of the user applications and the remote diagnosis management system.

13. The remote diagnosis management system of claim 9, wherein the at least one processor further executes a step of:
diagnosing the at least one state of each of the massage bath devices remotely.

14. The remote diagnosis management system of claim 9, wherein the at least one processor further executes a step of:
determining whether the remote trigger event is in a scope which the remote diagnosis management system is permitted to manage and/or configured to determine whether each of the massage bath devices is a target which is maintained by the remote diagnosis management system.

15. The remote diagnosis management system of claim 9, wherein the at least one processor further executes a step of:
remotely providing information related to the remote trigger event.

* * * * *